United States Patent
Johnson et al.

(10) Patent No.: US 8,741,354 B2
(45) Date of Patent: *Jun. 3, 2014

(54) COMPOSITE EXTRACELLULAR MATRIX MATERIALS AND MEDICAL PRODUCTS FORMED THEREFROM

(75) Inventors: Chad E. Johnson, West Lafayette, IN (US); David M. J. Ernst, Indianapolis, IN (US); Amy Overby, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 142 days.

This patent is subject to a terminal disclaimer.

(21) Appl. No.: 12/488,996

(22) Filed: Jun. 22, 2009

(65) Prior Publication Data

US 2009/0317469 A1 Dec. 24, 2009

Related U.S. Application Data

(60) Provisional application No. 61/074,441, filed on Jun. 20, 2008.

(51) Int. Cl.
*A61K 9/14* (2006.01)
*A61K 35/37* (2006.01)
*A61K 38/18* (2006.01)
*A61K 38/00* (2006.01)

(52) U.S. Cl.
USPC .......................... 424/550; 424/484; 424/489

(58) Field of Classification Search
CPC ..... A61L 27/3633; A61L 27/56; A61L 27/40; A61K 35/38
USPC ...................... 424/550, 484, 489; 514/7.6, 1.1
See application file for complete search history.

(56) References Cited

U.S. PATENT DOCUMENTS

| | | | |
|---|---|---|---|
| 3,329,572 A | 7/1967 | Malgouzou | |
| 3,551,560 A | 12/1970 | Thiele | |
| 4,511,653 A | 4/1985 | Play et al. | |
| 5,028,695 A | 7/1991 | Eckmayer et al. | |
| 5,523,291 A | 6/1996 | Janzen et al. | |
| 5,752,974 A | 5/1998 | Rhee | |
| 5,993,844 A | 11/1999 | Abraham et al. | |
| 6,090,996 A | 7/2000 | Li | |
| 6,162,247 A | 12/2000 | Weadock et al. | |
| 6,666,892 B2 | 12/2003 | Hiles et al. | |
| 6,753,181 B2 | 6/2004 | Atala | |
| 6,893,653 B2 | 5/2005 | Abraham et al. | |
| 6,986,735 B2 | 1/2006 | Abraham et al. | |
| 2002/0072806 A1 | 6/2002 | Buskirk et al. | |
| 2002/0099448 A1 | 7/2002 | Hiles et al. | |
| 2002/0103542 A1 | 8/2002 | Bilbo | |
| 2002/0106411 A1 | 8/2002 | Wironen et al. | |
| 2003/0013989 A1 | 1/2003 | Obermiller et al. | |
| 2003/0051735 A1 | 3/2003 | Pavcnik et al. | |
| 2003/0130746 A1 | 7/2003 | Ashworth et al. | |
| 2003/0167088 A1 | 9/2003 | Abraham et al. | |
| 2003/0206860 A1 | 11/2003 | Bleyer et al. | |
| 2004/0137042 A1 | 7/2004 | Hiles et al. | |
| 2005/0117339 A1 | 6/2005 | Pan | |
| 2006/0201996 A1 | 9/2006 | Hodde | |
| 2007/0112411 A1 | 5/2007 | Obermiller et al. | |
| 2007/0250177 A1 | 10/2007 | Bilbo | |
| 2007/0276507 A1 | 11/2007 | Bertram et al. | |
| 2008/0004657 A1 | 1/2008 | Obermiller et al. | |
| 2008/0063680 A1 | 3/2008 | Hiles et al. | |
| 2008/0145395 A1 | 6/2008 | Hiles et al. | |
| 2008/0145397 A1 | 6/2008 | Hiles et al. | |
| 2008/0248079 A1 | 10/2008 | Dempsey et al. | |
| 2008/0274184 A1 | 11/2008 | Hunt | |
| 2009/0318934 A1* | 12/2009 | Johnson et al. | ............... 606/111 |
| 2009/0326577 A1* | 12/2009 | Johnson et al. | ............... 606/213 |

FOREIGN PATENT DOCUMENTS

| | | |
|---|---|---|
| GB | 731501 | 6/1955 |
| JP | 2002-531181 | 9/2002 |
| JP | 2007-532153 | 11/2007 |
| WO | WO 00/32217 | 6/2000 |
| WO | WO 00/32250 | 6/2000 |
| WO | WO 03/002168 A1 | 1/2003 |
| WO | WO 2005020847 A2 * | 3/2005 |
| WO | WO 2005/097219 | 10/2005 |
| WO | WO 2006/119256 | 11/2006 |
| WO | WO 2006119256 A2 * | 11/2006 |
| WO | WO 2007/048099 | 4/2007 |
| WO | WO 2008/067085 | 6/2008 |
| WO | WO 2008/067085 A2 | 6/2008 |

OTHER PUBLICATIONS

Kallmes, D.F. et al., "In vivo evaluation of a new type I collagen hemostatic plug for high-risk, large-core biopsies," J. Vasc Interv Radiol. Jul.-Aug. 1998; 9(4):656-9.

Patel, Rupa et al., "Use of Fibrin Glue and Gelfoam to Repair Collecting System Injuries in a Porcine Model: Implications for the Technique of Laparoscopic Partial Nephrectomy," Journal of Endourology, vol. 17, No. 9, Nov. 2003.

Lisle, David A., et al. "Percutaneous Gelfoam Embolization of Chronic Enterocutaneous Fistulas: Report of Three Cases". Diseases of the Colon & Rectum, vol. 50, No. 2, Dec. 2006.

Maluf-Fiho, F. et al. "Enscopic Treatment of Esophagogastric Fistulae with an Acellular Matrix" Gastrointestinal Endoscopy, Elsevier, NL, vol. 59, No. 5, Apr. 2004, p. 151, XP004854594 abstract.

Schultz D J et al: "Porcine small intestine submucosa as a treatment for enterocutaneous fistulas" Journal of the American College of Surgeons, College, Chicago, IL, US, vol. 194, No. 4, Apr. 2002, pp. 541-543.

Shah, A. M., et al. "Bronchoscopic closure of bronchopleural fistula using gelfoam" abstract. Journal of Association of Physicians of India, 2004, vol. 52, no JUIN, pp. 508-509.

* cited by examiner

*Primary Examiner* — Abigail Fisher

(74) *Attorney, Agent, or Firm* — Woodard, Emhardt, Moriarty, McNett & Henry LLP

(57) ABSTRACT

Described in certain aspects are composite extracellular matrix material products including expanded collagenous materials in combination with non-expanded collagenous materials. Methods for their preparation and use are also disclosed. Certain expanded collagenous materials can be prepared by treating a first collagenous material with an alkaline substance under conditions effective to expand the first collagenous material, and recovering the expanded material. Expanded materials can exhibit beneficial persistence and tissue generation characteristics when implanted, and can be used in the formation of highly porous medical implant bodies which can be compressed to fractions of their original volume and will thereafter substantially recover their original volume.

22 Claims, 2 Drawing Sheets

COMPOSITE EXTRACELLULAR MATRIX MATERIALS AND MEDICAL PRODUCTS FORMED THEREFROM

REFERENCE TO RELATED APPLICATION

This application claims the benefit of U.S. Provisional Patent Application No. 61/074,441, filed Jun. 20, 2008, which is hereby incorporated herein in its entirety.

BACKGROUND

The present invention relates generally to improved extracellular matrix materials and, in certain aspects, to physically modified extracellular matrix materials, medical devices prepared therefrom, and uses thereof.

Biomaterials have been used in a variety of medical applications, including joint repair and replacement; periodontal reconstruction; repair or replacement of injured, diseased or malformed bones and tissues; wound healing; and the treatment of burns and diabetic ulcers. Extracellular matrix (ECM) materials, including those derived from submucosa and other tissues, are known tissue graft materials used in these medical applications. See, e.g., U.S. Pat. Nos. 4,902,508, 4,956,178, 5,281,422, 5,372,821, 5,554,389, 6,099,567, and 6,206,931. These materials are typically derived from a variety of biological sources including, for example, small intestine, stomach, the urinary bladder, skin, pericardium, dura mater, fascia, and the like.

Challenges remain in obtaining finished medical products derived from harvested animal ECM materials that possess the necessary physical properties as well as biological performance properties when implanted in patients. Accordingly, there remain needs for improved and alternative biomaterials and medical products, as well as methods for preparing and using them.

SUMMARY

In certain of its aspects, the present invention features unique collagenous matrix materials that exhibit beneficial properties relating to implant persistence, tissue generation, compressivity and/or expansivity, and/or other physical or biological properties, and to methods for their preparation and use. Desirable matrix materials comprise a denatured, expanded extracellular matrix material and possess an ability to persist when implanted and encourage the ingrowth of vascular structures into the matrix.

In one embodiment, the invention provides a bioactive composite extracellular matrix material product comprising a dried body formed with an extracellular matrix material that has been treated with an alkaline medium under conditions effective to produce an expanded extracellular matrix material, and particles of a bioactive extracellular matrix material entrapped within the dried body, with the particles of bioactive extracellular matrix material retaining at least one bioactive component, such as a growth factor, from a source tissue for the particulate extracellular matrix material. Methods for preparing such bioactive composites are also provided, and can include preparing a mixture including a liquid, the expanded extracellular matrix material and a particulate extracellular matrix material, and drying the mixture to form a bioactive, composite extracellular matrix material construct.

In another embodiment of the invention, provided is a composite extracellular matrix material product comprising an extracellular matrix sheet material and a dried material adhered to the extracellular matrix sheet material, with the dried material formed from an extracellular matrix material that has been contacted with an alkaline medium to form an expanded extracellular matrix material. Methods for preparing such composites are provided and can include casting a flowable, wet preparation of the expanded extracellular matrix material against an extracellular matrix sheet to form a wet composite, and drying the wet composite so as to form a dried composite.

In another embodiment of the invention, provided is a composite extracellular matrix material product comprising an extracellular matrix material and a dried material associated with the extracellular matrix material, with the dried material formed from an expanded extracellular matrix material. Methods for preparing such composites are provided and can include forming the expanded extracellular matrix material and associating the expanded extracellular matrix material with another extracellular matrix material, wherein the other extracellular matrix material can be in any suitable form.

In yet another embodiment, the present invention provides a composite extracellular matrix material product. The product includes a first extracellular matrix material in contact with a second, expanded extracellular matrix material.

Additional aspects as well as features and advantages of the invention will be apparent to those of ordinary skill in the art from the descriptions herein.

DETAILED DESCRIPTION

Figure 1A:
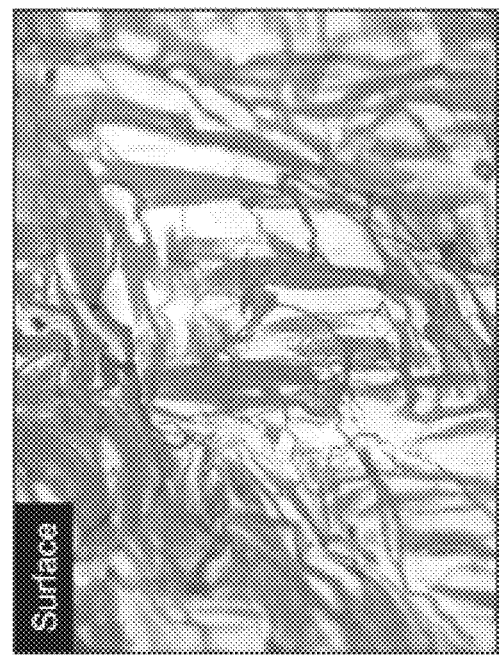
FIG. 1A depicts a micrograph taken at 100× magnification of a surface view of an expanded small intestinal submucosa material.

For the purposes of promoting an understanding of aspects of the invention, reference will now be made to certain embodiments and specific language will be used to describe the same. It will nevertheless be understood that no limitation of the scope of the invention is thereby intended. Any alterations and further modifications in the illustrative materials, constructs or methods described herein, and further applications of the principles of the invention as illustrated herein, are contemplated as would normally occur to one skilled in the art to which the invention pertains.

As disclosed above, certain embodiments of the invention involve composite extracellular matrix products that include an expanded extracellular matrix material in combination with another extracellular matrix material, and methods for their preparation and use.

Inventive products and methods are disclosed by which modified physical characteristics are imparted to extracellular matrix materials by controlled contact with an alkaline substance. Notably, such treatment can be used to promote substantial expansion (i.e. greater than about 20% expansion) of the extracellular matrix material. In accordance with certain aspects of the invention, this expanded material is processed into a variety of useful medical materials and devices. In certain embodiments, it is preferred to expand the material to at least about 2, at least about 3, at least about 4, at least about 5, or even at least about 6 times its original bulk volume. It will be apparent to one skilled in the art that the magnitude of expansion is related to the concentration of the alkaline substance, the exposure time of the alkaline substance to the material, and temperature, among others. These factors can be varied through routine experimentation to achieve a material having the desired level of expansion, given the disclosures herein.

A collagen fibril is comprised of a quarter-staggered array of tropocollagen molecules. The tropocollagen molecules themselves are formed from three polypeptide chains linked together by covalent intramolecular bonds and hydrogen bonds to form a triple helix. Additionally, covalent intermolecular bonds are formed between different tropocollagen molecules within the collagen fibril. Frequently, multiple collagen fibrils assemble with one another to form collagen fibers. It is believed that the addition of an alkaline substance to the material as described herein will not significantly disrupt the intramolecular and intermolecular bonds, but will denature the material to an extent that provides to the material a processed thickness that is at least twice the naturally-occurring thickness. In this regard, denaturation of the collagenous material to the extent described above allows for the production of a novel collagenous matrix material. The collagenous matrix material comprises a sterile, processed collagenous matrix material derived from a collagenous animal tissue layer, the collagenous animal tissue layer has a naturally-occurring thickness and includes a network of collagen fibrils having naturally-occurring intramolecular cross links and naturally-occurring intermolecular cross links. The naturally-occurring intramolecular cross links and naturally-occurring intermolecular cross links have been retained in the sterile, processed collagenous matrix material sufficiently to maintain the sterile, collagenous matrix material as an intact collagenous sheet material, and the collagen fibrils as they occur in the intact collagenous sheet material are denatured to an extent that provides to the intact collagenous sheet material a processed thickness that is substantially greater (i.e. at least about 20% greater) than, and preferably at least twice the naturally-occurring thickness of, the collagenous animal tissue layer.

Turning now to the figures, FIGS. 1A-D depict surface and cross-sectional views of both an expanded and a non-expanded extracellular matrix material sheet (porcine small intestine submucosa) wherein collagen has been stained such that its content and structure can be visualized. The four micrographs shown are as follows: (1A) the surface of the expanded ECM sheet material, (1B) the surface of a non-expanded ECM sheet material, (1C) a cross section of the expanded ECM sheet material, and (1D) a cross section of the non-expanded ECM sheet material. As shown in the micrographs, the surface and cross section views of the non-expanded material exhibit a tightly bound collagenous network whereas the same views of an expanded material exhibit a denatured, but still intact, collagenous network which has resulted in the expansion of the material.

In addition to causing expansion of a remodelable collagenous material, the application of an alkaline substance can alter the collagen packing characteristics of the material as illustrated in FIGS. 1A-D. Altering such characteristics of the material can be caused, at least in part, by the disruption of the tightly bound collagenous network. A non-expanded remodelable collagenous material having a tightly bound collagenous network typically has a continuous surface that is substantially uniform even when viewed under magnification, e.g. 100× magnification as shown in the Figures. Conversely, an expanded remodelable collagenous material typically has a surface that is quite different in that the surface is typically not continuous but rather presents collagen strands or bundles in many regions that are separated by substantial gaps in material between the strands or bundles. Consequently, an expanded remodelable collagenous material typically appears more porous than a non-expanded remodelable collagenous material. Moreover, the expanded remodelable collagenous material can be demonstrated as having increased porosity, e.g. by measuring its permeability to water or other fluid passage. The more foamy and porous structure of an expanded remodelable collagenous material can allow the material to be easily cast into a variety of foam shapes for use in the preparation of medical materials and devices. It can further allow for the compression and subsequent expansion of the material, which is useful, for example, when the material needs to be loaded into a deployment device for delivery into a patient. Once delivered, the material can expand to its original form.

As noted above, a non-expanded remodelable collagenous ECM material can typically comprise a variety of bioactive components including, for example, growth factors, glycoproteins, glycosaminoglycans, proteoglycans, nucleic acids, and lipids. Treating the material with an alkaline substance under conditions as described herein can significantly reduce, if not completely eliminate, these bioactive components from the material. Indeed, the treatment of the remodelable collagenous material with an alkaline substance can result in a remodelable collagenous material which is substantially devoid of growth factors, glycoproteins, glycosaminoglycans, proteoglycans, nucleic acids, and lipids. Accordingly, the treatment of a remodelable collagenous material with an alkaline substance as described herein can cause the material to expand to at least about twice its original volume, can alter the surface and/or porosity characteristics of the material, and can deplete the material of certain bioactive components. In some embodiments, this is accomplished while maintaining the material as an intact collagenous sheet, wherein the sheet can be further processed into any of a variety of medical materials and/or devices. Further, the remodelable collagenous material, such as an ECM sheet, can be treated with the alkaline medium so as to expand it as described herein, while the material retains an amount of a growth factor such as FGF-2, or another bioactive component such as fibronectin and/or heparin, that is/are native to the source tissue for the ECM or other collagenous material.

In certain embodiments, selected bioactive components that were previously removed from the remodelable collagenous material can be returned to the material. For example, the present invention provides an expanded remodelable collagenous material, which is substantially devoid of nucleic acids and lipids, but which has been replenished with one or more growth factors, glycoproteins, glycosaminoglycans, or proteoglycans or combinations thereof. These bioactive components can be returned to the material by any suitable method. For instance, in certain forms, a tissue extract containing these components can be prepared and applied to an expanded remodelable collagenous material. In one embodiment, the expanded remodelable collagenous material form is incubated in a tissue extract for a sufficient time to allow the bioactive components contained therein to associate with the expanded remodelable collagenous material. The tissue extract may, for example, be obtained from non-expanded remodelable collagenous tissue of the same type used to prepare the expanded material. Other means for returning or providing bioactive components to an expanded remodelable collagenous material include spraying, impregnating, dipping, etc. as known in the art. By way of example, an expanded remodelable collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, an expanded remodelable collagenous material may be replenished with other biological components such as heparin, heparin sulfate, hyaluronic acid, fibronectin and the like. Thus, generally speaking, an expanded remodelable collagenous material may include a bioactive component that induces, directly or indirectly, a cellular response such as a change in cell morphology, proliferation, growth, protein or gene expression.

The preparation of submucosa extracts is described in, for example, U.S. Pat. No. 6,375,989. Briefly, a submucosa extract can be prepared by the addition of an extraction excipient, such as urea, guanidine, sodium chloride, magnesium chloride, or a surfactant, to a submucosa tissue to isolate bioactive components from the tissue. The bioactive components are then separated from the extraction excipient. In one preferred embodiment, a submucosa extract is prepared by mixing submucosa tissue with a phosphate buffered solution, such as phosphate buffered saline (PBS). This mixture is processed into a slurry as buffer circulation and physical pressure are applied. The bioactive components present in the tissue are drawn into solution and subsequently isolated from the slurry. The bioactive submucosa extract is then formed by separating the extracted bioactive components in the solution from the slurry using art-recognized procedures such as dialysis and/or chromatographic techniques. Preferably, the extraction solution is dialyzed to reduce or remove the concentration of extraction excipients to provide a solution of the extracted bioactive components. Any source of submucosa tissue can be used to prepare a submucosa extract. Moreover, similar extraction techniques can be applied to other remodelable ECM materials to provide biologically active extracts for use in the invention.

The nature and quantity of the bioactive components contained in the submucosa or other extracellular matrix (ECM) extract is dependent on the nature and composition of the extraction excipients used for the extraction solution. Thus, for example, 2 M urea in a pH 7.4 buffer provides an extracted submucosa fraction enriched for basic fibroblast growth factor and fibronectin, while 4 M guanidine in the same buffer provides an extracted submucosa fraction enriched for a compound exhibiting an activity profile for TGF-beta. Use of other extraction excipients provides bioactive extracts comprising proteoglycans, glycoproteins and glycosaminoglycans such as heparin, heparin sulfate, hyaluronic acid, chondroitin sulfate A and chondroitin sulfate B.

In addition or as an alternative to the inclusion of native bioactive components, such as those provided in a submucosa or other ECM extract, non-native bioactive components including those synthetically produced by recombinant technology or other methods, may be incorporated into the expanded remodelable collagenous material. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the expanded remodelable collagenous materials used in the invention include, for example, antibiotics, thrombus-promoting substances such as blood clotting factors, e.g. thrombin, fibrinogen, and the like. As with the bioactive components previously described, these substances may be applied to the expanded remodelable collagenous material as a premanufactured step, immediately prior to the procedure (e.g. by soaking the material in a solution containing a suitable antibiotic such as cefazolin), or during or after engraftment of the material in the patient.

The expanded remodelable collagenous material may also exhibit an angiogenic character and thus be effective to induce angiogenesis in a host engrafted with the material. Angiogenic growth factors are well known in the art and include, for example, angiogenin, angiopoietin-1, Del-1, fibroblast growth factors (both acidic and basic), follistatin, granulocyte colony-stimulating factor, hepatocyte growth factor, interleukin-8 (IL-8), leptin, midkine, placental growth factor, platelet derived growth factor (PDGF), pleiotrophin, proliferin, transforming growth factors (both alpha and beta), tumor necrosis growth factor, and vascular endothelial growth factor (VEGF). Angiogenesis is the process through which the body makes new blood vessels to generate increased blood supply to tissues. Thus, angiogenic materials, when contacted with host tissues, promote or encourage the formation of new blood vessels. Methods for measuring in vivo angiogenesis in response to biomaterial implantation have recently been developed. For example, one such method uses a subcutaneous implant model to determine the angiogenic character of a material. See, C. Heeschen et al., *Nature Medicine* 7 (2001), No. 7, 833-839. When combined with a fluorescence microangiography technique, this model can provide both quantitative and qualitative measures of angiogenesis into biomaterials. C. Johnson et al., *Circulation Research* 94 (2004), No. 2, 262-268.

Expanded remodelable collagenous materials, as well as tissue extracts as described herein, are prepared, for example, from collagenous materials isolated from a suitable tissue source from a warm-blooded vertebrate, and especially a mammal. Such isolated collagenous material can be processed so as to have remodelable properties and promote cellular invasion and ingrowth. Suitable remodelable materials can be provided by collagenous extracellular matrix (ECM) materials possessing biotropic properties.

Suitable bioremodelable materials can be provided by collagenous extracellular matrix materials (ECMs) possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane, all of which can be derived for example from porcine, ovine or bovine tissue sources. These and other similar animal-derived tissue layers can be expanded and processed as described herein. Suitable submucosa materials for these purposes include, for instance, intestinal submucosa, including small intestinal submucosa, stomach submucosa, urinary bladder submucosa, and uterine submucosa.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

In order to prepare an expanded remodelable collagenous material, the material is preferably treated with a disinfecting agent so as to produce a disinfected, expanded remodelable collagenous material. Treatment with a disinfecting agent can be done either prior to or after isolation of the remodelable collagenous material from the tissue source or can be done either prior to or after expansion. In one preferred embodiment, the tissue source material is rinsed with a solvent, such as water, and is subsequently treated with a disinfecting agent prior to delamination. It has been found that by following this post-disinfection-stripping procedure, it is easier to separate the remodelable collagenous material from the attached tissues as compared to stripping the remodelable collagenous material prior to disinfection. Additionally, it has been discovered that the resultant remodelable collagenous material in its most preferred form exhibits superior histology, in that there is less attached tissue and debris on the surface compared to a remodelable collagenous material obtained by first delaminating the submucosa layer from its source and then disinfecting the material. Moreover, a more uniform remodelable collagenous material can be obtained from this process, and a remodelable collagenous material having the same or similar physical and biochemical properties can be obtained more consistently from each separate processing run. Importantly, a highly purified, substantially disinfected remodelable collagenous material is obtained by this process. In this regard, one embodiment of the invention provides a method for preparing an expanded remodelable collagenous material. The method comprises providing a tissue source including a remodelable collagenous material, disinfecting the tissue source, isolating the remodelable collagenous material from the tissue source, and contacting the disinfected remodelable collagenous material with an alkaline substance under conditions effective to expand the remodelable collagenous material to at least about two times its original volume, thereby forming the expanded remodelable collagenous material. Upon formation of the expanded remodelable collagenous material, the material can be further processed into medical materials and/or devices, or can be stored, e.g. in high purity water at 4° C., for later use.

Preferred disinfecting agents are desirably oxidizing agents such as peroxy compounds, preferably organic peroxy compounds, and more preferably peracids. As to peracid compounds that can be used, these include peracetic acid, perpropioic acid, or perbenzoic acid. Peracetic acid is the most preferred disinfecting agent for purposes of the present invention. Such disinfecting agents are desirably used in a liquid medium, preferably a solution, having a pH of about 1.5 to about 10, more preferably a pH of about 2 to about 6, and most preferably a pH of about 2 to about 4. In methods of the present invention, the disinfecting agent will generally be used under conditions and for a period of time which provide the recovery of characteristic, purified submucosa materials as described herein, preferably exhibiting a bioburden of essentially zero and/or essential freedom from pyrogens. In this regard, desirable processes of the invention involve immersing the tissue source or isolated remodelable collagenous material (e.g. by submersing or showering) in a liquid medium containing the disinfecting agent for a period of at least about 5 minutes, typically in the range of about 5 minutes to about 40 hours, and more typically in the range of about 0.5 hours to about 5 hours.

When used, peracetic acid is desirably diluted into about a 2% to about 50% by volume of alcohol solution, preferably ethanol. The concentration of the peracetic acid may range, for instance, from about 0.05% by volume to about 1.0% by volume. Most preferably, the concentration of the peracetic acid is from about 0.1% to about 0.3% by volume. When hydrogen peroxide is used, the concentration can range from about 0.05% to about 30% by volume. More desirably the hydrogen peroxide concentration is from about 1% to about 10% by volume, and most preferably from about 2% to about 5% by volume. The solution may or may not be buffered to a pH from about 5 to about 9, with more preferred pH's being from about 6 to about 7.5. These concentrations of hydrogen peroxide can be diluted in water or in an aqueous solution of about 2% to about 50% by volume of alcohol, most preferably ethanol.

With respect to the alkaline substance used to prepare an expanded remodelable collagenous material, any suitable alkaline substance generally known in the art can be used. Suitable alkaline substances can include, for example, salts or other compounds that that provide hydroxide ions in an aqueous medium. Preferably, the alkaline substance comprises sodium hydroxide (NaOH). The concentration of the alkaline substance that is added to the material can be in the range of about 0.5 to about 4 M. Preferably, the concentration of the alkaline substance is in the range of about 1 to about 3M. Additionally, the pH of the alkaline substance will typically range from about 8 to about 14. In preferred embodiments, the alkaline substance will have a pH of from about 10 to about 14, and most preferably of from about 12 to about 14.

In addition to concentration and pH, other factors such as temperature and exposure time will contribute to the extent of expansion. In this respect, it is preferred that the exposure of the remodelable collagenous material to the alkaline substance is performed at a temperature of about 4 to about 45° C. In preferred embodiments, the exposure is performed at a temperature of about 25 to about 37° C., with 37° C. being most preferred. Moreover, the exposure time can range from about several minutes to about 5 hours or more. In preferred embodiments, the exposure time is about 1 to about 2 hours. In a particularly preferred embodiment, the remodelable collagenous material is exposed to a 3 M solution of NaOH having a pH of 14 at a temperature of about 37° C. for about 1.5 to 2 hours. Such treatment results in the expansion of a remodelable collagenous material to at least about twice its original volume. As indicated above, these processing steps can be modified to achieve the desired level of expansion.

In addition to an alkaline substance, a lipid removal agent can also be added to a remodelable collagenous material either prior to, in conjunction with, or after the addition of the alkaline substance. Suitable lipid removal agents include, for example, solvents such as ether and chloroform, or surfactants. Other suitable lipid removal agents will be apparent to those of ordinary skill in the art. Accordingly, the lipid removal agents listed herein serve only as examples, and are therefore in no way limiting.

In preferred embodiments, the expanded remodelable collagenous materials, as well as tissue extracts containing bioactive components that can optionally be added to an expanded remodelable collagenous material, are sterilized using conventional sterilization techniques including tanning with glutaraldehyde, formaldehyde tanning at acidic pH, ethylene oxide treatment, propylene oxide treatment, gas plasma sterilization, gamma radiation, and peracetic acid sterilization. A sterilization technique which does not significantly alter the remodelable properties of the expanded remodelable collagenous material is preferably used. Moreover, in embodiments where the expanded remodelable collagenous material includes a native or non-native bioactive component, the sterilization technique preferably does not significantly alter the bioactivity of the expanded remodelable collagenous material. Preferred sterilization techniques include exposing the extract to peracetic acid, low dose gamma irradiation (2.5 mRad) and gas plasma sterilization.

The expanded remodelable collagenous materials of the invention can be provided in any suitable form, including a flowable aqueous composition (e.g., a fluidized composition), a powder, a gel, a sponge, one or more sheets, or a cast body. One or more of these forms of an expanded material can be combined with a non-expanded extracellular matrix material. As well, the non-expanded material can be prepared in any of these forms so long as the expanded and non-expanded material can be combined to form a composite extracellular matrix material. In one embodiment, the expanded remodelable collagenous material is processed into a fluidized composition, for instance using techniques as described in U.S. Pat. No. 5,275,826. In this regard, solutions or suspensions of the expanded remodelable collagenous material can be prepared by comminuting and/or digesting the material with a protease (e.g. trypsin or pepsin), for a period of time sufficient to solubilize the material and form substantially homogeneous solution. The expanded remodelable collagenous material is desirably comminuted by, tearing, cutting, grinding, shearing (e.g. combined with a liquid and sheared in a blender), or the like, which can generate random fragments of the expanded remodelable collagenous material to provide a randomly fragmented form. The expanded remodelable collagenous material typically has a spongy and porous structure, so these techniques may not be needed to the extent they would be needed to solubilize a non-expanded remodelable collagenous material. Grinding the material in a frozen or freeze-dried state is advantageous, although good results can be obtained as well by subjecting a suspension of pieces of the material to treatment in a high speed blender and dewatering, if necessary, by centrifuging and decanting excess waste. The comminuted material can be dried, for example freeze dried, to form a particulate. The particulate can be used itself to treat a patient, e.g., for trauma wounds, or can be hydrated, that is, combined with water or buffered saline and optionally other pharmaceutically acceptable excipients, to form a fluidized, expanded remodelable collagenous material, e.g. having a viscosity of about 2 to about 300,000 cps at 25° C. The higher viscosity graft compositions can have a gel or paste consistency.

In one embodiment of the invention, a particulate remodelable collagenous material formed separately from the expanded remodelable collagenous material can be combined with a fluidized, expanded remodelable collagenous material. Such particulate remodelable collagenous materials can be prepared by cutting, tearing, grinding, shearing or otherwise comminuting a remodelable collagenous source material, which can provide random fragments of the remodelable collagenous material. Such a material can be an expanded material or a non-expanded material. As well, the expanded or non-expanded particulate can include one or more additives to promote hemostasis. Suitable such additives include, as examples, calcium alginate or zeolite. Such additives can include adhesive properties that allow the particulate to adhere to a desired location (e.g., tissue surface) after implantation. For example, a particulate ECM material having an average particle size of about 50 microns to about 500 microns may be included in the fluidized, expanded remodelable collagenous material, more preferably about 100 microns to about 400 microns. The remodelable collagenous particulate can be added in any suitable amount relative to the fluidized, expanded remodelable collagenous material, with preferred remodelable collagenous particulate to fluidized, expanded remodelable collagenous material weight ratios (based on dry solids) being about 0.1:1 to about 200:1, more preferably in the range of 1:1 to about 100:1. The inclusion of such remodelable collagenous particulates in the ultimate fluidized, expanded remodelable collagenous material can serve to provide additional material that can function to provide bioactivity to the composition (e.g. itself including growth factors or other bioactive components as discussed herein), serve as scaffolding material for tissue ingrowth and/or promote expansion of a compressed remodelable collagenous material.

As well, a fluidized composition prepared from an expanded remodelable collagenous material can optionally be dried to form a sponge solid or foam material. In certain embodiments, when a particulate of a non-expanded material is combined with a fluidized composition as described herein, the particulate will be added to the fluidized composition prior to drying such that the particulate becomes embedded within the dried, expanded material. Dry sponge or foam form materials of the invention prepared by drying expanded remodelable collagenous material gels, including those combined with non-expanded particulate material, can be used, for example, in wound healing, tissue reconstructive applications, occlusive applications, hemostatic applications, in the culture of cells, and in a variety of additional applications including those disclosed elsewhere herein.

An expanded remodelable collagenous material of the invention can also be used in body wall repair including, for example, in the repair of abdominal wall defects such as hernias, using techniques analogous to those described in *Ann. Plast. Surg.*, 1995, 35:3740380; and *J. Surg. Res.*, 1996, 60:107-114. In such applications, preferred materials of the invention are in sheet form and promote favorable organization, vascularity and consistency in the remodeled tissue. Sheet form expanded remodelable collagenous material can for example be formed by stretching an expanded material over a backing board, freezing the material, and lyophilizing the material. In dermatological applications, an expanded remodelable collagenous material can be used in the repair of partial or full thickness wounds and in dermal augmentation using general grafting techniques which are known to the art and literature (see, e.g. *Annals of Plastic Surgery* 1995, 35:381-388). In addition, in the area of burn treatment, it is generally known to provide a dermal substitute onto which cultured epidermal grafts (preferably cultured epidermal autografts, or CEA's) are transplanted. Such cultured grafts have typically involved transplanting keratinocytes and/or fibroblasts onto the dermal substitute. In accordance with the present invention, the purified, expanded remodelable collagenous material can be used as the dermal substitute, for example in sheet form, and the CEA accordingly transplanted onto the material. In one mode of practicing this aspect of the invention, the expanded remodelable collagenous material of the invention can be used to prepare a wound care matrix. In one preferred embodiment, a wound care matrix can be prepared by providing a tissue source including a remodelable collagenous material, disinfecting the tissue source, isolating the remodelable collagenous material from the tissue source, contacting the disinfected remodelable collagenous material with an alkaline substance under conditions effective to expand the remodelable collagenous material to at least about two times its original volume, forming the expanded remodelable collagenous material into one or more sheets and lyophilizing the material to form the wound care matrix. Alternatively, the one or more sheets can be vacuum pressed or sutured together as known in the art to form the wound care matrix. Such embodiments can also involve coupling or otherwise physically associating sheet form expanded material with sheet form non-expanded extracellular matrix material, for example by making a multilaminate device including these two types of materials.

In embodiments of the invention where an expanded remodelable collagenous ECM material is provided in sheet form, the material can have a thickness in the range of about 0.2 mm to about 2 mm, more preferably about 0.4 mm to about 1.5 mm, and most preferably about 0.5 mm to about 1 mm. If necessary or desired, a multilaminate material can be used. For example, a plurality of (i.e. two or more) layers of an expanded remodelable collagenous ECM material can be bonded or otherwise coupled together to form a multilaminate structure. Illustratively, two, three, four, five, six, seven, or eight or more layers of an expanded remodelable collagenous material can be bonded together to provide a multilaminate material. In certain embodiments, two to six expanded, submucosa-containing layers isolated from intestinal tissue of a warm-blooded vertebrate, particularly small intestinal tissue, are bonded together to provide a medical material. Porcine-derived small intestinal tissue is preferred for this purpose. In alternative embodiments, one or more sheets of a non-expanded collagenous material (e.g., submucosa) can be bonded or otherwise coupled to one or more sheets of an expanded remodelable collagenous material. Any number of layers can be used for this purpose and can be arranged in any suitable fashion with any number of layers of a non-expanded remodelable collagenous material bonded to any number of layers of an expanded remodelable collagenous material. The layers of collagenous tissue can be bonded together in any suitable fashion, including dehydrothermal bonding under heated, non-heated or lyophilization conditions, using adhesives as described herein, glues or other bonding agents, crosslinking with chemical agents or radiation (including UV radiation), or any combination of these with each other or other suitable methods.

A variety of dehydration-induced bonding methods can be used to fuse portions of multi-layered medical materials together. In one preferred embodiment, the multiple layers of material are compressed under dehydrating conditions. The term "dehydrating conditions" can include any mechanical or environmental condition which promotes or induces the removal of water from the multi-layered medical material. To promote dehydration of the compressed material, at least one of the two surfaces compressing the matrix structure can be water permeable. Dehydration of the material can optionally be further enhanced by applying blotting material, heating the matrix structure or blowing air, or other inert gas, across the exterior of the compressing surfaces. One particularly useful method of dehydration bonding multi-layered medical materials is lyophilization, e.g. freeze-drying or evaporative cooling conditions.

Another method of dehydration bonding comprises pulling a vacuum on the assembly while simultaneously pressing the assembly together. This method is known as vacuum pressing. During vacuum pressing, dehydration of the multi-layered medical materials in forced contact with one another effectively bonds the materials to one another, even in the absence of other agents for achieving a bond, although such agents can be used while also taking advantage at least in part of the dehydration-induced bonding. With sufficient compression and dehydration, the multi-layered medical materials can be caused to form a generally unitary laminate structure.

It is advantageous in some aspects of the invention to perform drying operations under relatively mild temperature exposure conditions that minimize deleterious effects upon the multi-layered medical materials of the invention, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions. It will be understood that the above-described means for coupling two or more multi-layered medical materials together to form a laminate can also apply for coupling together one or more layers of peritoneum and fascia when these layers are isolated independent from one another.

In addition to the above, the expanded remodelable collagenous material of the present invention can be used to prepare a molded or shaped construct for example a sponge useful as an occluder device or biopsy plug. The method for preparing such device comprises providing an expanded remodelable collagenous material, comminuting the expanded material, casting the expanded remodelable collagenous material into a shape, and freezing and lyophilizing the cast, expanded remodelable collagenous material to form the construct. Freezing can be done at a temperature of about −80° C. for about 1 to about 4 hours, and lyophilization can be performed for about 8 to about 48 hours. The material used to prepare the construct can be an expanded remodelable collagenous material that has been replenished with one or more bioactive components and/or supplemented with a particulate, non-expanded remodelable collagenous material. The expanded remodelable collagenous material and any other components can be cast into any shape desired and will typically be shaped by a skilled artisan to occlude a particular area in need of occlusion. In preferred embodiments, a biopsy plug is formed and is used, for example, to fill a void in a tissue (e.g., organ tissue) after surgery. When a sponge form construct is prepared, the lyophilized, expanded remodelable collagenous material can be compressed and loaded into a deployment device for delivery into a patient. Once delivered, the device can expand to occlude the area in which it was deployed. Suitable deployment devices will be generally known to those of ordinary skill in the art and include, for example, delivery catheters and the like.

In certain embodiments, it may be desirable to include one or more additives into the expanded remodelable collagenous material to promote re-expansion of a compressed material. Any suitable additive can be used. Suitable additives include, for example, salts, such as sodium chloride, sodium acetate, sodium bicarbonate, sodium citrate, calcium carbonate, potassium acetate, potassium phosphate; hydrogel and water-swelling polymers, such as alginate, polyhydroxethyl methacralate, polyhydroxypropyl methacrylate, polyvinyl alcohol, polyethylene glycol, carboxymethyl cellulose, polyvinyl pyrrolidone; proteins, such as gelatin and SIS particulate; acids and bases, such as acetic acid and ascorbic acid; super-absorbing polymers and gelling agents, such as polyacrylic acid, pectin, polygalacturonic acid, polyacrylic acid-co-acrylamide, polyisobutylene-co-maleic acid; monosaccharides, polysaccharides, and derivatives thereof, such as dextran, glucose, fructose, sucrose, sucrose ester, sucrose laurate, galactose, chitosan, poly-N-acetyl glucosamine, heparin, hyaluronan, and chrondroitin sulfate; as well as other potential additives, such as guanidine HCl, urea, hydroxyethyl cellulose, sodium cholate, sodium taurocholate, ionic detergents (e.g., SDS), and non-ionic detergents (e.g., Triton). In preferred embodiments, the one or more additives includes a biocompatible salt such as sodium chloride, sodium acetate, or sodium bicarbonate; polyethylene glycol (e.g. MW 6000), and/or SIS or other ECM particulate.

The one or more additives can provide a variety of functions, including promoting expansion of the material once implanted into a patient. For example, a sponge form expanded remodelable collagenous material including one or more additives can be compressed and placed into a delivery device. Compression of the material allows the material to be more easily transferred to a patient. Upon delivery, the material can expand to at least about its original size prior to compression. This is typically done with an occluder device or a biopsy plug where it is desirable for the material to have a smaller diameter prior to delivery and expand upon delivery. Such additives can be included in the remodelable collagenous material to expand the material at a faster rate than would otherwise be achievable in the absence of the one or more additives. For example, one or more additives can be included with a compressed remodelable collagenous material so as to promote the re-expansion of the material back to its original size within at least about 30 seconds, 45 seconds, 1 minute, 2 minutes, 3 minutes, 4 minutes, or even about least about 5 minutes after implantation. As with the bioactive components previously described, these additives may be applied to the expanded remodelable collagenous material as a premanufactured step, immediately prior to the procedure (e.g. by soaking the material in a solution containing a suitable antibiotic such as cefazolin), or during or after engraftment of the material in the patient.

In certain embodiments, an expanded remodelable collagenous material, in any form, can be crosslinked. An expanded remodelable collagenous material can be crosslinked either before or after it is formed into a medical device (e.g., a composite extracellular matrix material product), or both. Increasing the amount (or number) of crosslinkages within the material or between two or more layers of the material can be used to enhance its strength. However, when a remodelable material is used, the introduction of crosslinkages within the material may also affect its resorbability or remodelability. Consequently, in certain embodiments, a remodelable collagenous material will substantially retain its native level of crosslinking, or the amount of added crosslinkages within the medical device will be judiciously selected depending upon the desired treatment regime. In many cases, the material will exhibit remodelable properties such that the remodeling process occurs over the course of several days or several weeks. In certain preferred embodiments, the remodeling process occurs within a matter of about 5 days to about 12 weeks. With regard to a sponge form construct, crosslinking of a compressed construct may promote re-expansion of the construct after implantation into a patient.

With regard to compressible/expandable plugs, sponges or other constructs as described herein, expansion additives and/or crosslinking can be used to impart desirable compression/re-expansion properties. In preferred forms, the constructs are capable of volumetric compression when dry at a ratio of at least 10:1 (i.e. the compressed form occupies no more than 10% of its original, relaxed and unexpanded volume), more preferably at a ratio of at least 20:1. At the same time, in preferred forms, the compressed constructs are capable of re-expansion to substantially their original volume (e.g. at least about 80% of their original volume, more preferably at least 90%, and most preferably at least 95%) within about 30 seconds when delivered in their dry, compressed form into a volume of water.

For use in the present invention, introduced crosslinking of the expanded remodelable collagenous material may be achieved by photo-crosslinking techniques, or by the application of a crosslinking agent, such as by chemical crosslinkers, or by protein crosslinking induced by dehydration or other means. Chemical crosslinkers that may be used include for example aldehydes such as glutaraldehydes, diimides such as carbodiimides, e.g., 1-ethyl-3-(3-dimethylaminopropyl)carbodiimide hydrochloride (EDC), diisocyanates such as hexamethylene-diisocyanate, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

When a multi-layered laminate material is contemplated, the layers of the laminate can be additionally crosslinked to bond multiple layers of a multi-layered medical material to one another. Cross-linking of multi-layered medical materials can also be catalyzed by exposing the matrix to UV radiation, by treating the collagen-based matrix with enzymes such as transglutaminase and lysyl oxidase, and by photo-crosslinking. Thus, additional crosslinking may be added to individual layers prior to coupling to one another, during coupling to one another, and/or after coupling to one another.

The medical materials, constructs and devices of the invention can be provided in sterile packaging suitable for medical materials and devices. Sterilization may be achieved, for example, by irradiation, ethylene oxide gas, or any other suitable sterilization technique, and the materials and other properties of the medical packaging will be selected accordingly.

In certain embodiments, the invention provides compressible medical foam products, and methods for their preparation. The medical foam products include a dried, compressible foam body formed with an extracellular matrix solid material that has been treated with an alkaline medium under conditions effective to produce an expanded extracellular matrix collagen material. In such forms, the compressible foam body can further include a particulate of a non-expanded extracellular matrix material as described herein, preferably one that retains one or more bioactive components, such as a growth factor, with which it naturally occurs. The foam body can have introduced chemical crosslinks sufficient to increase the resiliency of the foam body. Absent crosslinking, foam bodies produced from the expanded extracellular matrix collagen material possess resiliency, but for certain applications, including for example hemostatic plug applications, it has been discovered that increased resiliency is desired for certain uses. The introduction of collagen crosslinks, for example with chemical crosslinkers such as glutaraldehyde, carbodimides, or other chemical crosslinkers identified herein, has been found to significantly enhance the resiliency of the foam plugs, while leaving the compressible to a small size for delivery. Increased resiliency in turn provides additional compression upon adjacent tissues when the foam plugs are inserted in a compressed state and then allowed to expand in situ in a patient at a site at which hemostasis is desired. In specific inventive applications, crosslinked, resilient foam plugs as disclosed herein can be utilized to provide hemostasis at surgical sites, including biopsy sites. These biopsy or other surgical sites can be located within parenchymal organ tissues, such as those of a kidney, liver or spleen of a patient.

Thus, in certain forms of the invention, surgical methods are provided which include resecting tissue from a parenchymal organ such as a liver or kidney, and then implanting a crosslinked, resilient foam material as described herein, desirably a composite material as described herein, at the resection site so as to facilitate hemostasis. The resection can, as examples, occur as a part of a nephrectomy or hepatectomy, e.g. to removed cancerous or other diseased tissue, or as a part of a kidney or liver biopsy performed with a biopsy needle. In the case of minimally invasive surgical procedures such as laparoscopic resections, or needle biopsies, the crosslinked, resilient foam plug can be delivered from within a cannulated device such as a needle or catheter, and/or through a laparoscopic device. The resilient foam plug can be in a compressed state during delivery, and then allowed to expand once delivered to the surgical site. The expansion of the plug can compress the adjacent tissues to facilitate hemostasis. For these purposes, the expanded dimensions of the plug can provide a volume that is at least equal to or preferably greater than the volume of the biopsy or other surgical defect, to ensure compression of surrounding tissues by the delivered, expanded plug.

In other embodiments of the invention, methods are provided which include deploying a crosslinked, resilient foam material as described herein, preferably a composite material as described herein, at a site within a bodily vessel, for example an artery or a vein, so as to cause occlusion of the vessel and thereby stop the flow of fluid (e.g. blood) within the vessel. In the case of minimally invasive surgical procedures such as percutaneous procedures the crosslinked, resilient foam plug can be delivered from within a cannulated device such as a catheter or sheath. The resilient foam plug can be in a compressed state during delivery, and then allowed to expand once delivered from within the cannulated device to the desired occlusion site. The expansion of the plug can compress the walls of the vessel to facilitate occlusion. For these purposes, the expanded dimensions of the plug can be greater than the diameter of the vessel at the desired site of occlusion, to ensure outward compression against surrounding vessel walls by the delivered, expanded plug. Besides vascular vessels, other vessels that can be occluded in accordance with the invention include, for example, fallopian tube(s). Still further, other open tracts through patient tissue can be occluded with crosslinked, resilient foam plugs of the invention, including for example needle tracts (e.g. resultant of percutaneous entry to a vein or artery) and fistulas, such as anorectal fistulas, enterocutaneous fistulas, recto-vaginal fistulas, and others.

Crosslinked, resilient foam plugs can be prepared by a process that includes:

(a) contacting extracellular matrix material with an alkaline medium to form an expanded extracellular matrix material;

(b) washing the expanded extracellular matrix material;

(c) charging the expanded extracellular matrix material to a mold;

(d) lyophilizing the expanded extracellular matrix material in the mold to form a lyophilized extracellular matrix material foam;

(e) contacting the lyophilized extracellular matrix material foam with a chemical crosslinking agent to form a crosslinked extracellular matrix material foam; and (f) drying the crosslinked extracellular matrix material foam.

In such methods, the extracellular matrix material and chemical crosslinked agent can, for example, be selected from among any of those disclosed herein. The washing can suitably be conducted with an aqueous medium, such as saline or water. The drying can be conducted by any suitable method, including as examples air drying at ambient temperature, heated drying, or lyophilization. It is preferred to contact the extracellular matrix material with the chemical crosslinker after the formation of the lyophilized extracellular matrix material foam (e.g. as opposed to incorporating the chemical crosslinker in the material charged to the mold), as this has been found to provide more uniformly shaped crosslinked plugs that resist shrinkage. Further, in such preparative methods, the expanded extracellular matrix material can be comminuted prior to charging to the mold, forming expanded extracellular matrix fragments that will be incorporated within and will characterize the extracellular matrix foam material. In more preferred forms, the material is comminuted by shearing the material with a rotating blade, e.g. in a blender. For these purposes, it has been discovered that when utilizing an extracellular matrix material that is a harvested, deceullarized sheet, the sheet can be contacted with the alkaline medium under conditions sufficient to substantially reduce the tensile strength of the sheet, so that the sheet material is disrupted by the rotating blade. Without sufficient reduction of tensile strength, the sheet material can tend to wrap around the rotating blade, thus frustrating the process of comminution. For example, prior to comminution by the blade or otherwise, the sheet can be treated with the alkaline medium for a time and under conditions sufficient to reduce the tensile strength of the sheet to less than about 50% of its original tensile strength, more preferably to less than about 30% of its original tensile strength. Such methods can be practiced, for example, with harvested sheet-form ECM materials such as submucosa-containing sheets, e.g. obtained from small intestinal, stomach or bladder tissue, pericardial tissue, peritoneal tissue, fascia, dermal tissue, and other sheet-form ECM materials.

In certain embodiments described herein, a composite extracellular matrix material product can be prepared by coupling or otherwise associating an expanded extracellular matrix material with a non-expanded extracellular matrix material. The expanded and non-expanded materials can each be in any suitable form as described above so long as the two materials can be combined to form a composite extracellular matrix material product. In one embodiment of the invention, the composite product comprises a dried body formed with an extracellular matrix material that has been treated with an alkaline medium under conditions effective to produce an expanded extracellular matrix material and particles of a bioactive extracellular matrix material entrapped within said dried body, wherein the particles of bioactive extracellular matrix material retain at least one growth factor from a source tissue for the particulate extracellular matrix material. The composite products can be prepared by an inventive method that includes the steps of:

(a) contacting extracellular matrix material with an alkaline medium to form an expanded extracellular matrix material;

(b) washing the expanded extracellular matrix material;

(c) preparing a mixture including a liquid, the expanded extracellular matrix material and a particulate extracellular matrix material, the particulate extracellular matrix material retaining an amount of at least one growth factor from a source tissue for the particulate extracellular matrix material; and (d) drying the mixture to form a bioactive, composite extracellular matrix material construct.

In such composite products and preparative methods, the extracellular matrix material that is expanded, and the particulate extracellular matrix material, can, for example, be selected from among any of those disclosed herein. The washing can suitably be conducted with an aqueous medium, such as saline or water. The liquid for preparing the mixture can be any suitable liquid, preferably biocompatible, and typically an aqueous liquid such as water or saline. The drying step can be conducted by any suitable method, including as examples air drying at ambient temperature, heated drying, or lyophilization. Further, in such preparative methods, the expanded extracellular matrix material is desirably comminuted prior to or during the formation of the mixture. In more preferred forms, the material is comminuted by shearing the material with a rotating blade, e.g. in a blender, alone or in the presence of the bioactive particulate extracellular matrix material. Such methods can be practiced, for example, with harvested sheet-form ECM materials such as submucosa-containing sheets, e.g. obtained from small intestinal, stomach or bladder tissue, pericardial tissue, peritoneal tissue, fascia, dermal tissue, and other sheet-form ECM materials. The expanded ECM material and the bioactive particulate ECM material can be from the same ECM starting material or from different ECM starting materials. It has been discovered that the incorporation of the particulate ECM material can serve not only to enhance the bioactivity of the foam product, but also enhance the resiliency of the foam product.

Figure 2:
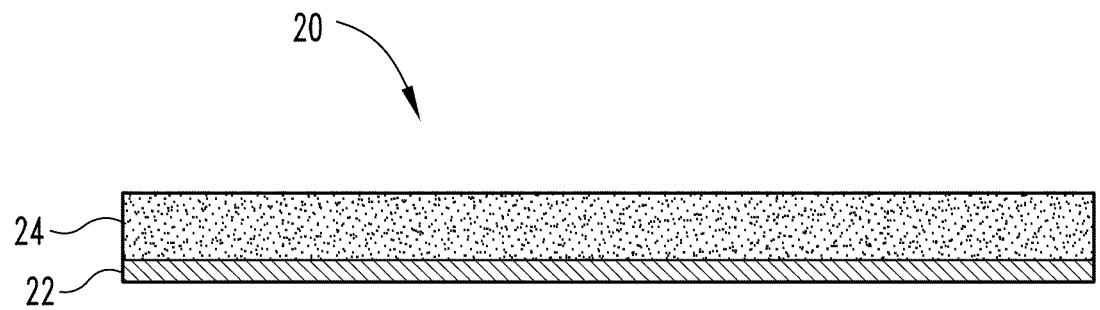
FIG. 2 provides a cross-section view of an illustrative composite extracellular matrix material product of the invention.
Figure 3:
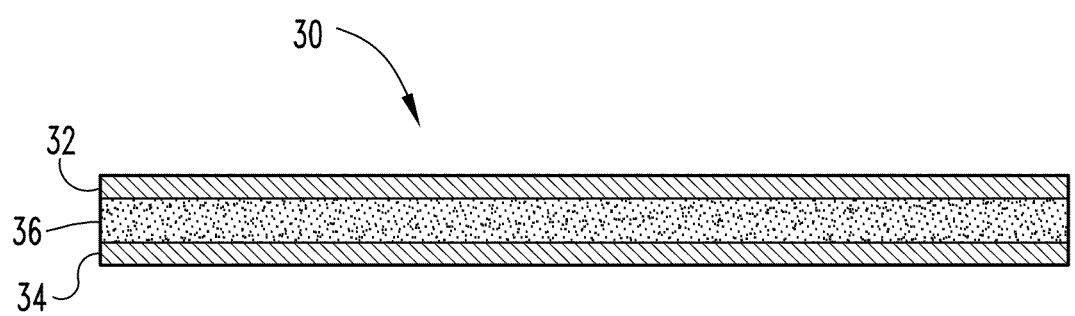
FIG. 3 provides a cross-section view of another illustrative composite extracellular matrix material product of the invention.
Figure 4:
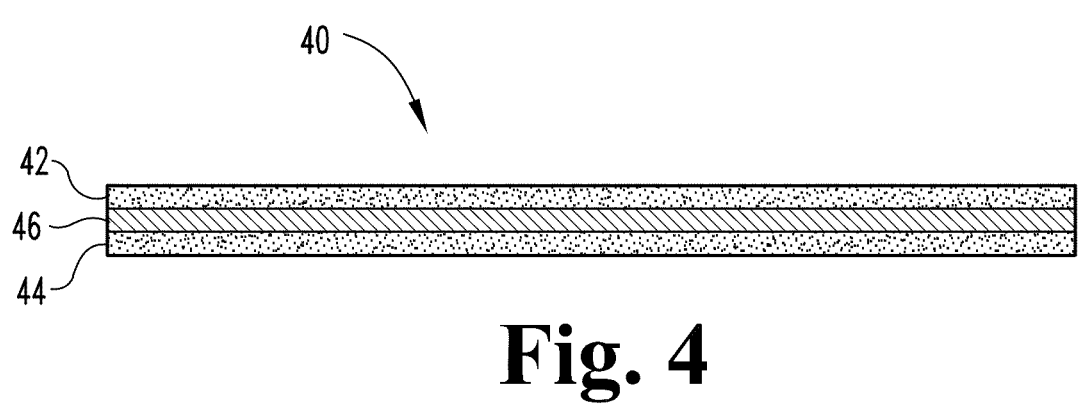
FIG. 4 provides a cross-section view of another illustrative composite extracellular matrix material product of the invention.

In additional embodiments, such as those illustrated in FIGS. 2-4, the invention provides composite extracellular matrix material products that include an extracellular matrix sheet material and a dried material adhered to the extracellular matrix sheet material, wherein the dried material is formed from an extracellular matrix material that has been contacted with an alkaline medium to form an expanded extracellular matrix material. Such composite products can be prepared by a method that includes the steps of:

(a) contacting extracellular matrix material with an alkaline medium to form an expanded extracellular matrix material;

(b) washing the expanded extracellular matrix material;

(c) casting a flowable, wet preparation of the expanded extracellular matrix material against an extracellular matrix sheet to form a wet composite; and (d) drying the wet composite so as to form a dried composite.

In such composite sheet-material products and preparative methods, the extracellular matrix material that is expanded, and the particulate extracellular matrix material, can, for example, be selected from among any of those disclosed herein. The washing can suitably be conducted with an aqueous medium, such as saline or water. The liquid for preparing the wet preparation can be any suitable liquid, preferably biocompatible, and typically an aqueous liquid such as water or saline. The drying step can be conducted by any suitable method, including as examples air drying at ambient temperature, heated drying, or lyophilization. Lyophilization is preferred as it forms a more porous, resilient foam material as compared to air drying or heated drying. Further, in such preparative methods, the expanded extracellular matrix material in the flowable, wet preparation is desirably comminuted. In more preferred forms, the material is comminuted by shearing the material with a rotating blade, e.g. in a blender. Such methods can be practiced, for example, with harvested sheet-form ECM materials such as submucosa-containing sheets, e.g. obtained from small intestinal, stomach or bladder tissue, pericardial tissue, peritoneal tissue, fascia, dermal tissue, and other sheet-form ECM materials. The expanded ECM material and the sheet-form ECM material can be from the same ECM starting material or from different ECM starting materials. The incorporation of the sheet-form ECM material can serve not only to enhance the bioactivity of the overall product, but can also provide a barrier material and/or suturable sheet attached to the dried expanded ECM material (e.g. foam). Illustratively, such constructs can be used to provide hemostasis to surgical sites or other injured tissue. In certain modes of practice, the construct can be placed against the bleeding tissue with the dried, expanded ECM material (especially a foam) against the bleeding tissue. The sheet-form ECM can then provide an additional barrier (besides the expanded ECM material) to protect the bleeding tissue, and or can provide a suturable sheet material which can be used to fix the construct in place, e.g. with sutures in strand or staple form. In specific uses, such constructs can be used to apply hemostasis to surgically-treated (e.g. subject to resection) or otherwise injured parenchymous organ tissue, such as liver or kidney tissue. In so doing, the dried, expanded ECM material is desirably pressed against the injured parenchymous tissue, and the sheet-form ECM material can optionally be used to fix the construct in place, as discussed above. These and other modes of practice with the composite sheet-form constructs will be apparent to those of ordinary skill in the art from the descriptions herein.

Turning now to specific embodiments, FIGS. 2-4 illustrate certain sheet form composite extracellular matrix sheet form products. FIG. 2. provides a composite extracellular matrix sheet form product 20. The composite extracellular matrix sheet form product 20 includes a sheet form of a non-expanded extracellular matrix material 22 associated with an expanded extracellular matrix material 24. It will be understood by a skilled artisan that any number of expanded material layers can be associated with any number of non-expanded layers. For example, FIG. 3 illustrates a composite extracellular matrix material product 30 including two sheets of a non-expanded extracellular matrix material 32 and 34 associated with a sheet of an expanded extracellular matrix material 36. The sheet of expanded extracellular matrix material 36 is sandwiched between the sheets of non-expanded extracellular matrix material 32 and 34. Similarly, multiple layers of an expanded extracellular matrix material can be combined with a layer of a non-expanded material. For example, FIG. 3 illustrates a composite extracellular matrix material product 40 including single layer of a non-expanded material 46 sandwiched between two sheets of an expanded extracellular matrix material 42 and 44. Such composite sheet form extracellular matrix material products can be prepared as described above.

For the purpose of promoting a further understanding of aspects of the present invention, the following specific examples are provided. It will be understood that these examples are not limiting of the present invention.

Example 1

Figure 1C:
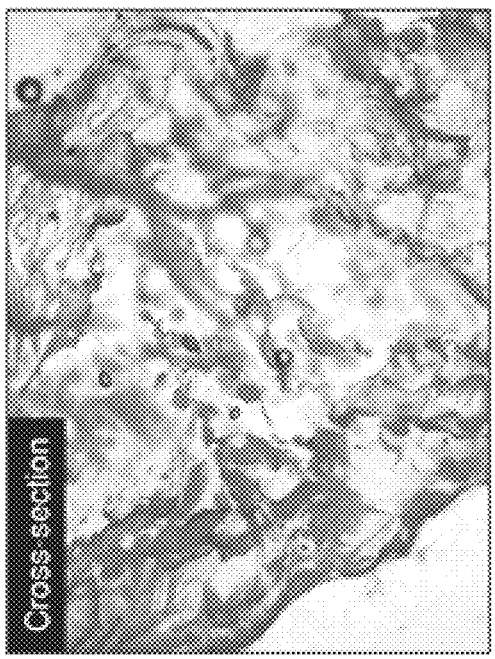
FIG. 1C depicts a micrograph taken at 100× magnification of a cross-section view of an expanded small intestinal submucosa material.
Figure 1B:
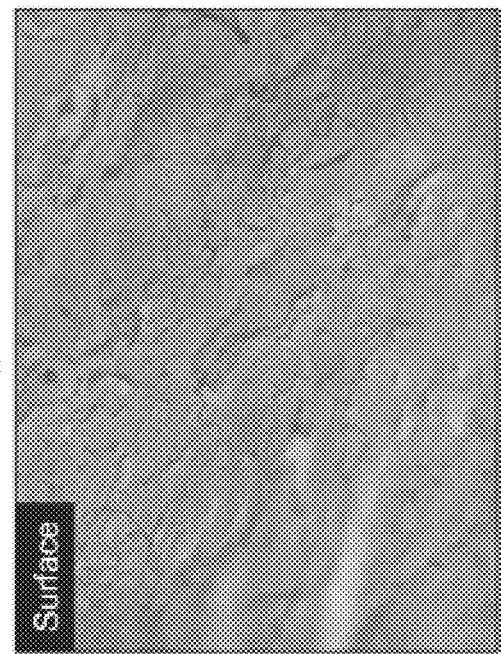
FIG. 1B depicts a micrograph taken at 100× magnification of a surface view of a non-expanded small intestinal submucosa material.
Figure 1D:
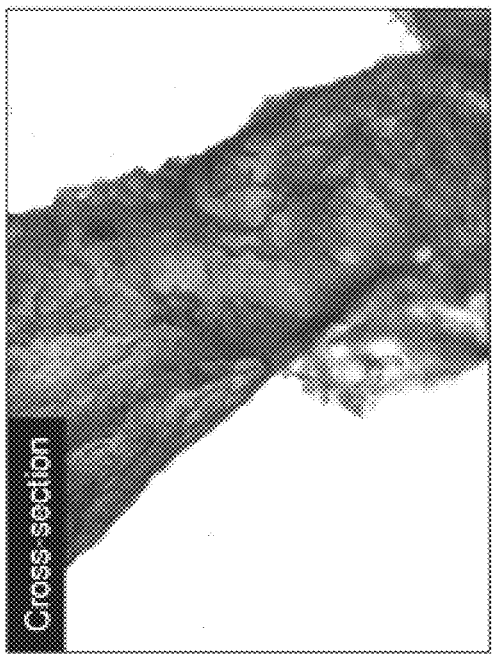
FIG. 1D depicts a micrograph taken at 100× magnification of a cross-section view of a non-expanded small intestinal submucosa material.

This example demonstrates the process used to prepare a disinfected small intestinal submucosa tissue (i.e., non-expanded SIS), which can subsequently be used in the preparation of various medical materials and devices. Surface and cross section micrographs of the material are depicted in FIGS. 1B and 1D.

A ten foot section of porcine whole intestine was extracted and washed with water. After rinsing, this section of submucosa intestinal collagen source material was treated for about two and a half hours in 0.2% peracetic acid by volume in a 5% by volume aqueous ethanol solution with agitation. Following the treatment with the peracetic acid solution, the submucosa layer was delaminated in a disinfected casing machine from the whole intestine. The resultant submucosa was then rinsed four (4) times with sterile water. A 1 cm by 1 cm section of this material was extracted and stained using a solution of direct red prepared by mixing 10 mg direct red in 100 mL high purity water. The section of material was stained for approximately 5 minutes. The stained material was washed twice with high purity water to remove any unbound stain. The stained material was placed on a glass slide and covered with a cover slip. A micrograph was taken (Olympus microscope) at 100× magnification of the surface of the material. A cross section of the material was then prepared and a similar micrograph was taken. The resulting micrograph was analyzed using Spot RT software. The surface and cross section micrographs are depicted in FIGS. 1B and 1D. Both the surface and cross section micrographs show a tightly bound collagenous matrix with no expansion.

Example 2

This example demonstrates the process used to prepare an expanded small intestinal submucosa tissue (i.e., expanded SIS), which can subsequently be used in the preparation of various medical materials and devices as described herein. Surface and cross section micrographs of the material are depicted in FIGS. 1A and 1C.

A ten foot section of porcine whole intestine was extracted and washed with water. After rinsing, this section of submucosa intestinal collagen source material was treated for about two and a half hours in 0.2% peracetic acid by volume in a 5% by volume aqueous ethanol solution with agitation. Following the treatment with peracetic acid, the submucosa layer was delaminated in a disinfected casing machine from the whole intestine. The resultant submucosa was then rinsed four (4) times with sterile water. 300 g of this material was soaked with agitation in 1 L of a 1M NaOH solution at 37° C. for 1 hour and 45 minutes. The material was removed and rinsed in a 1 L solution of high purity water for 5 minutes. This rinsing step was repeated 8 additional times. A 1 cm by 1 cm section of this material was extracted and stained using a solution of direct red prepared by mixing 10 mg direct red in 100 mL high purity water. The section of material was stained for approximately 5 minutes. The stained material was washed twice with high purity water to remove any unbound stain. The stained material was placed on a glass slide and covered with a cover slip. A micrograph was taken (Olympus microscope) at 100× magnification of the surface of the material. A cross section of the material was then prepared and a similar micrograph was taken. The resulting micrograph was analyzed using Spot RT software. The surface and cross section micrographs are depicted in FIGS. 1A and 1C. Both the surface and cross section micrographs show disruption of the tightly bound collagenous matrix and an expansion of the material.

As can be observed in FIGS. 1A-1D, both the surface view and the cross-section view of the non-expanded SIS show a tightly bound collagenous matrix whereby collagen content is substantially uniform throughout. Conversely, the surface view and cross-section view of the expanded SIS show a denatured collagenous network and an expansion of the material.

Example 3

This Example was performed to identify additives that can be included in an expanded remodelable collagenous material for purposes of promoting rapid re-expansion of the material after implantation into a patient.

An expanded remodelable material was prepared generally as described in Example 2. Briefly, a ten foot section of porcine whole intestine was extracted and washed with water. After rinsing, this section of submucosa intestinal collagen source material was treated for about two and a half hours in 0.2% peracetic acid by volume in a 5% by volume aqueous ethanol solution with agitation. Following the treatment with peracetic acid, the submucosa layer was delaminated in a disinfected casing machine from the whole intestine. The resultant submucosa was then rinsed four (4) times with sterile water. 300 g of this material was soaked with agitation in 1 L of a 3M NaOH solution at 37° C. for 2 hours. The material was removed and rinsed in a 1 L solution of high purity water for 15 minutes. After 15 minutes, 1 L of 0.2M acetic acid was added with agitation. After 15 minutes of agitation, the material was rinsed with 1 L of high purity water with shaking for 5 minutes. This rinsing step was repeated four (4) times for a total of five (5) rinses.

The rinsed material was mechanically agitated using the pulse setting of a blender to the extent that the blended material could be transferred using a disposable 25 mL pipette. Samples of the blended material were combined with a hand-held blender with the various additives as identified in Table 1. The samples were then cast into cylindrical molds, frozen at −80° C. for 5 hours, and lyophilized for 24 hours to yield 14 mm diameter cylindrical constructs ranging in length from about 15 mm to about 19 mm.

TABLE 1

| Additive Category | Screened Additives |
|---|---|
| Salts | Sodium chloride |
| | Sodium acetate |
| | Sodium bicarbonate |
| | Sodium citrate |
| | Calcium carbonate |
| | Potassium acetate |
| | Potassium phosphate |
| Hydrogels and Water Swelling Polymers | Alginate |
| | Polyhydroxyethyl methacralate |
| | Polyvinyl alcohol |
| | Polyethylene glycol |
| | Carboxymethyl cellulose |
| | Polyvinyl pyrrolidone |

TABLE 1-continued

| Additive Category | Screened Additives |
|---|---|
| Proteins | Gelatin |
|  | SIS particulate |
| Acids and Bases | Acetic acid |
|  | Ascorbic acid |
| Monosaccharides and Polysaccharides | Dextran |
|  | Glucose |
|  | Fructose |
| Superabsorbing Polymers and Gelling Agents | Polyacrylic acid |
|  | Polygalacturonic acid |
| Other Additives | Guanidine HCl |
|  | Urea |

At the time of testing, the initial sample diameter was recorded. All cylindrical samples were then compressed by hand to between 2.7 mm and 6.7 mm, and the final diameter of the compressed material was recorded. Approximately 20 mL of high purity water at room temperature was transferred into a weight boat. The compressed material was placed on the surface of the high purity water and submerged using forceps to expose all surfaces of the material to the high purity water. A digital timer was started at the time the sample was submerged. Visual assessment of the material was continuously conducted until the sample returned to the initial sample diameter as assessed through visual inspection. When the sample returned to the initial sample diameter, the timer was stopped and the expansion time recorded. Visual assessment was discontinued after 15 minutes for samples that did not return to the initial sample diameter in the time allotted. The results are summarized in Tables 2-8.

TABLE 2

| Additive | % Dry Weight of Dry Plug | Initial Diameter (mm) | Compressed Diameter (mm) | Expansion Time (min:sec) |
|---|---|---|---|---|
| Sodium chloride | 2.5 | 12 | 4.0 | 1:41 |
|  | 7.5 | 13 | 4.0 | >15:00* |
|  |  | 14 | 3.7 | >15:00* |
| Sodium acetate | 1.25 | 13 | 3.7 | 6:30 |
|  |  | 13 | 3.7 | 6:00 |
|  | 2.5 | 13 | 4.7 | 0:45 |
|  |  | 12 | 4.3 | 0:45 |
|  | 5.0 | 13 | 4.7 | 1:30 |
|  |  | 14 | 5.0 | 2:00 |
| Sodium bicarbonate | 2.5 | 13 | 4.0 | 2:00 |
|  |  | 13 | 4.3 | 1:15 |
|  | 5.0 | 13 | 6.7 | 3:00 |
|  |  | 13 | 5.0 | 1:20 |
| Sodium citrate | 2.5 | 14 | 5.3 | 8:00 |
|  |  | 14 | 5.0 | 8:00 |
|  | 5.0 | 14 | 5.0 | 12:00 |
|  |  | 14 | 4.7 | 12:00 |
| Calcium carbonate | 2.5 | 14 | 4.7 | >15:00* |
|  |  | 14 | 4.3 | >15:00* |
|  | 5.0 | 14 | 5.3 | 8:00 |
|  |  | 14 | 5.0 | 8:00 |
|  | 12.5 | 14 | 4.7 | >15:00* |
|  |  | 14 | 4.7 | >15:00* |
| Potassium acetate | 2.5 | 13 | 5.3 | >15:00* |
|  |  | 13 | 4.7 | >15:00* |
|  | 5.0 | 14 | 4.3 | >15:00* |
|  |  | 14 | 4.3 | >15:00* |
| Potassium phosphate | 2.5 | 10 | 3.0 | 13:00 |
|  |  | 10 | 3.0 | 13:00 |
|  | 5.0 | 13 | 3.0 | 14:00 |
|  |  | 12 | 3.3 | 11:00 |

*Indicates control sample behaved atypically, suggesting the expansion time may not be representative of the additive tested.

TABLE 3

| Additive | % Dry Weight of Dry Plug | Initial Diameter (mm) | Diameter (mm) | Expansion Time (min:sec) |
|---|---|---|---|---|
| Alginate | 2.5 | 13 | 3.0 | >15:00 |
| Polyhydroxyethyl methacralate | 2.5 | 13 | 3.0 | 8:50 |
|  |  | 13 | 2.7 | 8:58 |
| Polyvinyl alcohol | 2.5 | 14 | 3.0 | 5:48 |
| Polyethylene glycol (MW 400) | 7.5 | 14 | 2.3 | >15:00* |
|  |  | 14 | 2.3 | >15:00* |
| Polyethylene glycol (MW 6000) | 2.5 | 13 | 3.0 | 3:22 |
| Carboxymethyl cellulose | 2.5 | 13 | 3.7 | 7:03 |
| Polyvinyl pyrrolidone | 2.5 | 14 | 3.3 | 5:25 |

*Indicates control sample behaved atypically, suggesting the expansion time may not be representative of the additive tested.

TABLE 4

| Additive | % Dry Weight of Dry Plug | Initial Diameter (mm) | Diameter (mm) | Expansion Time (min:sec) |
|---|---|---|---|---|
| Gelatin (100 bloom) | 2.5 | 13 | 3.0 | >15:00 |
| 45-90 µm SIS particulate | 5.0 | 14 | 4.7 | 2:38 |
|  |  | 13 | 4.7 | 2:35 |
|  | 10.0 | 13 | 5.0 | 1:32 |
|  |  | 13 | 4.7 | 1:20 |
|  | 20.0 | 14 | 6.3 | 0:37 |
|  |  | 14 | 6.0 | 0:52 |
| 90-150 µm SIS particulate | 5.0 | 14 | 3.7 | 2:30 |
|  |  | 13 | 3.7 | 2:00 |
|  | 10.0 | 13 | 4.7 | 2:30 |
|  |  | 14 | 5.0 | 3:00 |
|  | 20.0 | 13 | 5.3 | 1:30 |
|  |  | 13 | 6.3 | 1:42 |
| 150-200 µm SIS particulate | 5.0 | 14 | 4.0 | 2:45 |
|  |  | 14 | 4.3 | 2:50 |
|  | 10.0 | 14 | 4.7 | 2:30 |
|  |  | 13 | 4.3 | 2:25 |
|  | 20.0 | 13 | 5.7 | 1:55 |
|  |  | 13 | 5.0 | 2:35 |

TABLE 5

| Additive | % Dry Weight of Dry Plug | Initial Diameter (mm) | Diameter (mm) | Expansion Time (min:sec) |
|---|---|---|---|---|
| Ascorbic acid | 2.5 | 14 | 3.0 | >15:00* |
|  |  | 14 | 3.0 | >15:00* |
|  | 5.0 | 14 | 3.0 | >15:00* |
|  |  | 14 | 3.3 | >15:00* |

*Indicates control sample behaved atypically, suggesting the expansion time may not be representative of the additive tested.

TABLE 6

| Additive | % Dry Weight of Dry Plug | Initial Diameter (mm) | Diameter (mm) | Expansion Time (min:sec) |
|---|---|---|---|---|
| Polyacrylic acid | 2.5 | 13 | 3.3 | 8:24 |
|  |  | 13 | 3.0 | 8:07 |
| Polygalacturonic acid | 2.5 | 13 | 3.0 | 4:00 |
|  |  | 13 | 3.0 | 4:35 |

TABLE 7

| Additive | % Dry Weight of Dry Plug | Initial Diameter (mm) | Diameter (mm) | Expansion Time (min:sec) |
|---|---|---|---|---|
| Dextran | 2.5 | 13 | 3.0 | 5:15 |
|  |  | 13 | 3.3 | 4:16 |
| Glucose | 2.5 | 14 | 3.7 | >15:00* |
|  |  | 14 | 3.7 | >15:00* |
|  | 5.0 | 14 | 3.7 | >15:00* |
|  |  | 14 | 3.0 | >15:00* |
| Fructose | 2.5 | 14 | 3.7 | >15:00* |
|  |  | 14 | 4.0 | >15:00* |
|  | 5.0 | 14 | 3.3 | >15:00* |
|  |  | 14 | 3.7 | >15:00* |

*Indicates control sample behaved atypically, suggesting the expansion time may not be representative of the additive tested.

TABLE 8

| Additive | % Dry Weight of Dry Plug | Initial Diameter (mm) | Compressed Diameter (mm) | Expansion Time (min:sec) |
|---|---|---|---|---|
| Guanidine HCl | 2.5 | 14 | 3.0 | 4:16 |
|  |  | 14 | 2.7 | 4:50 |
| Urea | 5.0 | 14 | 3.0 | >15:00 |
|  |  | 14 | 3.3 | >15:00 |

Based on these results, preferred additives include sodium chloride, sodium acetate, sodium bicarbonate, polyethylene glycol (MW 6000), and small intestinal submucosa particulate Example 4

This Example was performed to measure the angiogenic activity of various forms of an expanded remodelable collagenous material as described herein.

An expanded remodelable material was prepared generally as described in Example 3. Briefly, a ten foot section of porcine whole intestine was extracted and washed with water. After rinsing, this section of submucosa intestinal collagen source material was treated for about two and a half hours in 0.2% peracetic acid by volume in a 5% by volume aqueous ethanol solution with agitation. Following the treatment with peracetic acid, the submucosa layer was delaminated in a disinfected casing machine from the whole intestine. The resultant submucosa was then rinsed four (4) times with sterile water. 300 g of this material was soaked with agitation in 1 L of a 3M NaOH solution at 37° C. for 2 hours. The material was removed and rinsed in a 1 L solution of high purity water for 15 minutes. After 15 minutes, 1 L of 0.2M acetic acid was added with agitation. After 15 minutes of agitation, the material was rinsed with 1 L of high purity water with shaking for 5 minutes. This rinsing step was repeated four (4) times for a total of five (5) rinses. Three different forms of expanded remodelable collagenous material were prepared from this material: (1) blended expanded remodelable collagenous material, (2) expanded remodelable collagenous material in conjunction with a submucosa particulate (1:10), and (3) 4-layered lyophilized sheet form expanded remodelable collagenous material.

These materials from groups (1) and (2) were cast into a thick film of approximately 1 mm in thickness, frozen at −80° C. for 5 hours and lyophilized for 24 hours. Ten 15 mm discs were cut from each group using a disc punch to form test samples. Nylon filters with 0.22 μm pores were sewn on to the top and bottom of each disc. Low temperature ethylene oxide sterilization was used for each sample. Samples were implanted subcutaneously into the dorsal flanks of mice. After anesthesia using Ketamine (87 mg/kg) and Xylazine (13 mg/kg), a small incision was made on the posterior neck of the mouse, and a dorsal subcutaneous cavity was created using blunt dissection with hemostats. This was followed by sample placement and closure of the incision with 4 interrupted stitches of 5-0 suture. Six mice per group underwent disc implantation. The implant remained in the mice for a period of 3 weeks followed by probing for capillary formation.

Mice were sacrificed using a double dose of anesthesia to ensure intact flow in vasculature. While the heart was still beating, the chest cavity was exposed, vena cava severed, and 10 mL of heparized saline injected into the left ventricle using a 23 ga butterfly infusion set to exsanguinate the mouse. After transferring syringes (while maintaining infusion needle in left ventricle), 4 mL of a fluorescent microsphere (yellow-green, 0.1 μm diameter, Molecular Probes, F-8803) suspension (1:20 dilution of stock suspension) was injected through the left ventricle resulting in perfusion of the entire vasculature. Care was taken to ensure no bubbles were introduced during the injections, as bubbles will cause micro-emboli obstructing consistent perfusion. Samples were collected with gentle dissection and gross removal of the fibrous capsule. A positive control of hind limb muscle was also collected at this point to confirm proper perfusion. Collected samples and controls were placed on ice in a closed container to maintain tissue integrity (mainly moistness). Microvasculature was imaged using a confocal microscope (Biorad), $\lambda_{ex}$=488 nm & $\lambda_{em}$=530 nm, along the edge of the samples in the area of greatest vascular infiltration. Further, vasculature of the positive controls, hind limb muscle, was imaged to confirm good perfusion.

In addition to the fluorescence microangiography described above, samples were collected, placed in histology cassettes, and submerged in 10% buffered formalin (Fisher). Histological sectioning and staining with hematoxilin and eosin were performed by Portland Tissue Processing. Images of H&E stained sections of the disc edge for each sample were taken using a microscope (Olympus) with a 10× objective.

Each of the samples from all three test groups showed some angiogenic activity when fluorescence microangiography was performed. Similarly, the histology analysis confirmed that all three sample groups had some vascular and cellular ingrowth.

This Example demonstrates that various forms of an expanded remodelable collagenous material each exhibit angiogenic activity in vivo.

Example 5

This Example was performed to investigate the angiogenic activity of a crosslinked, expanded remodelable collagenous material as described herein.

An expanded remodelable material was prepared generally as described in Example 3. Briefly, a ten foot section of porcine whole intestine was extracted and washed with water. After rinsing, this section of submucosa intestinal collagen source material was treated for about two and a half hours in 0.2% peracetic acid by volume in a 5% by volume aqueous ethanol solution with agitation. Following the treatment with peracetic acid, the submucosa layer was delaminated in a disinfected casing machine from the whole intestine. The resultant submucosa was then rinsed four (4) times with sterile water. 300 g of this material was soaked with agitation in 1 L of a 3M NaOH solution at 37° C. for 2 hours. The material was removed and rinsed in a 1 L solution of high purity water for 15 minutes. After 15 minutes, 1 L of 0.2M acetic acid was added with agitation. After 15 minutes of agitation, the material was rinsed with 1 L of high purity water with shaking for 5 minutes. This rinsing step was repeated four (4) times for a total of five (5) rinses. Approximately 250 mL of the expanded remodelable collagenous material was placed into a blender along with 250 mL of high purity water. This mixture was pulsed 10 times for 1 second each pulse followed by a 45 second blend. The resulting material was cast into a 5×10 cm mold having a thickness of approximately 1 mm. This mold was placed in a freezer at −80° C. for 5 hours followed by lyophilization for 24 hours. 15 mm disc samples were cut from the resulting blended sheet.

To form the crosslinked samples, the samples formed above were combined with 200 mL of 50 mM EDC crosslinking solution in a shallow glass dish. The disc with samples were submerged under solution and placed onto a rotating shaker for 24 hours at room temperature. Each sample was then rinsed with 200 mL of high purity water squeezing five (5) times. This step was repeated four (4) times for a total of five (5) rinses. The rinsed material was then lyophilized for approximately 8 hours.

Each of the samples showed some angiogenic activity when fluorescence microangiography was performed. Similarly, the histology analysis confirmed that all three sample groups had some vascular and cellular ingrowth. Indeed, the crosslinked material had robust angiogenesis (1442+108 μm) and was still present in plug form. The plug expanded at explant indicating that the crosslinked material was substantive and did not collapse after implantation. Moreover, there were no signs of systemic or local toxicity and no evidence of increased local inflammation in these samples.

This Example further demonstrates that a crosslinked form of an expanded remodelable collagenous material can exhibit angiogenic activity in vivo.

Example 6

This Example was performed to determine the FGF-2 content of an expanded remodelable collagenous material as described herein.

An expanded remodelable material was prepared generally as described in Example 3. Briefly, a ten foot section of porcine whole intestine was extracted and washed with water. After rinsing, this section of submucosa intestinal collagen source material was treated for about two and a half hours in 0.2% peracetic acid by volume in a 5% by volume aqueous ethanol solution with agitation. Following the treatment with peracetic acid, the submucosa layer was delaminated in a disinfected casing machine from the whole intestine. The resultant submucosa was then rinsed four (4) times with sterile water. 300 g of this material was soaked with agitation in 1 L of a 3M NaOH solution at 37° C. for 2 hours. The material was removed and rinsed in a 1 L solution of high purity water for 15 minutes. After 15 minutes, 1 L of 0.2M acetic acid was added with agitation. After 15 minutes of agitation, the material was rinsed with 1 L of high purity water with shaking for 5 minutes. This rinsing step was repeated four (4) times for a total of five (5) rinses.

Two lots of material described above were prepared with one lot used per group. One lot of material was made into single-layer lyophilized sheets, and the other material was mixed with small intestinal submucosa particulate (~150 μm) and made into single-layer lyophilized sheets. Three (3) samples were cut (2 cm×2 cm) from each lot resulting in three (3) samples per group. Each sample was weighed and its weight was recorded. Individual samples were placed in 1.5 mL eppendorf tubes and 400 μl of sterile phosphate buffered saline (PBS) was added to each tube. Tubes with samples were centrifuged at 12000 g for 5 minutes at 4° C. The resulting supernatant was diluted to 1:1 with 1×PBS. Samples were assayed in duplicate for FGF-2 content using R&D Systems FGF-2 ELISA kits per manufacturer's instructions.

The resulting content of FGF-2 was calculated by dividing the FGF-2 content by the weights of the samples. The means measured FGF-2 content in the sheet form expanded remodelable collagenous material was 0 pg/g. The mean measured FGF-2 content in expanded remodelable collagenous material including a submucosa particulate was 4500 pg/g+1600 pg/g.

This Example demonstrates that an expanded remodelable collagenous material in sheet form, prepared and tested as described in this example, contains no detectable levels of FGF-2, and that FGF-2 can be provided back to an expanded remodelable collagenous material by virtue of the inclusion of a submucosa particulate into the material.

The use of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. In addition, all publications cited herein are indicative of the abilities of those of ordinary skill in the art and are hereby incorporated by reference in their entirety as if individually incorporated by reference and fully set forth.

What is claimed is:

1. A composite extracellular matrix material product, comprising:
   a dried compressed foam body that expands when wetted, said dried compressed body formed by compression of a cast body having introduced chemical crosslinks, said cast body including a first extracellular matrix material that has been treated with an alkaline medium under conditions effective to produce an expanded extracellular matrix material having a tensile strength of less than 50% of the tensile strength of an original tensile strength of the extracellular matrix material and particles of a second extracellular matrix material entrapped within said cast body, wherein said particles increase a rate of expansion of said dried compressed body when wetted, and further wherein said introduced chemical crosslinks are sufficient to increase the resiliency of the foam body.

2. The product of claim 1, wherein said alkaline medium comprises an aqueous medium containing a source of hydroxide ions.

3. The product of claim 1, wherein said expanded extracellular matrix material has a volume of at least 120% that of its original volume.

4. The product of claim 1, wherein said dried body and said particles are derived from a decellularized tissue layer.

5. The product of claim 4, wherein said decellularized tissue layer comprises submucosa.

6. The product of claim 1, wherein said dried body containing the particles of a bioactive extracellular matrix material is crosslinked.

7. The product of claim 1, wherein said dried body is comprised of a dry lyophilized material.

8. The product of claim 1, wherein product further comprises at least one added biologically active agent.

9. The product of claim 8, wherein said at least one biologically active agent includes one or more of a growth factor, glycoprotein, glycosaminoglycan, or proteoglycan.

10. A composite extracellular matrix material product, comprising:
a compressed body formed by chemically crosslinking a construct and compressing the construct after said chemically crosslinking, said construct comprising:
a first extracellular matrix material containing at least one retained native growth factor from a source tissue for the first extracellular matrix material; and
a dried material adhered to the first extracellular matrix material, said dried material expandable when wetted and formed from a second extracellular matrix material that has been contacted with an alkaline medium under conditions effective to form an expanded extracellular matrix material having a tensile strength that is less than 50% of an original tensile strength of the extracellular matrix material.

11. The product of claim 10, wherein said alkaline medium comprises an aqueous medium containing a source of hydroxide ions.

12. The product of claim 10, wherein said expanded extracellular matrix material has a volume of at least 120% that of its original volume.

13. The product of claim 10, wherein said first extracellular matrix material and said dried material are derived from a decellularized tissue layer.

14. The product of claim 13, wherein said decellularized tissue layer comprises submucosa.

15. The product of claim 10, wherein said expanded extracellular matrix material is comprised of a dry lyophilized material.

16. The product of claim 10, wherein said product further comprises at least one added biologically active agent.

17. The product of claim 10, wherein said at least one biologically active agent includes one or more of a growth factor, glycoprotein, glycosaminoglycan, or proteoglycan.

18. The product of claim 10, wherein the first extracellular matrix material is a sheet material.

19. A composite extracellular matrix material product, comprising:
a compressed body formed by chemically crosslinking a construct and compressing the construct after said chemically crosslinking, said construct comprising:
a first extracellular matrix material containing at least one retained native growth factor from a source tissue for the first extracellular matrix material; and
a second extracellular matrix material, wherein the second extracellular matrix material is dried and expands when wetted, and wherein the second extracellular matrix material is an extracellular matrix material that has been expanded under conditions effective to reduce its tensile strength to less than 50% of an original tensile strength of the extracellular matrix material.

20. The product of claim 19, wherein the first extracellular matrix material also retains native glycoproteins, glycosaminoglycans and proteoglycans from the source tissue.

21. The product of claim 20, wherein the expanded extracellular matrix material retains naturally-occurring intramolecular crosslinks and naturally-occurring intermolecular crosslinks sufficient to maintain the expanded extracellular matrix material as an expanded sheet material.

22. The product of claim 21, wherein the expanded sheet material is in randomly fragmented form.

* * * * *